United States Patent [19]

Peterson et al.

[11] Patent Number: 5,133,901

[45] Date of Patent: Jul. 28, 1992

[54] SYSTEM AND METHOD FOR ON-LINE MONITORING AND CONTROL OF HEAVY METAL CONTAMINATION IN SOIL WASHING PROCESS

[75] Inventors: Steven H. Peterson, Murrysville; Edward J. Lahoda, Edgewood Borough; David C. Grant, Gibsonia; Edward F. Sverdrup, North Huntingdon; Thomas V. Congedo, Edgewood; John Bartko, State College; Robert E. Witkowski, West Mifflin; Arthur L. Wolfe, Murrysville; William D. Partlow, Forest Hills, all of Pa.; Michael C. Skriba, Irvine, Calif.

[73] Assignee: Westinghouse Electric Corp., Pittsburgh, Pa.

[21] Appl. No.: 663,962

[22] Filed: Mar. 1, 1991

[51] Int. Cl.$^5$ .............................. G21F 19/00
[52] U.S. Cl. ................... 252/626; 210/660; 210/681; 210/682; 209/3.2; 209/576; 209/456
[58] Field of Search .............. 209/2, 3.1, 3.2, 552, 209/576, 579, 586, 589, 456, 457; 252/626, 625; 210/660, 681, 682

[56] References Cited

U.S. PATENT DOCUMENTS

| | | | |
|---|---|---|---|
| 3,204,097 | 8/1965 | Moffat et al. | 250/255 |
| 3,443,092 | 5/1969 | Carr-Brion et al. | 250/265 |
| 3,832,545 | 8/1974 | Bartko | 250/312 |
| 3,889,112 | 6/1975 | Holmes et al. | 250/265 |
| 3,942,003 | 3/1976 | Apenberg et al. | 250/255 |
| 4,125,769 | 11/1978 | Marten et al. | 250/272 |
| 4,134,012 | 1/1979 | Smallbone et al. | 250/272 |
| 4,194,634 | 3/1980 | Kelly | 209/589 |
| 4,388,530 | 6/1983 | Lubecki et al. | 378/45 |
| 4,450,576 | 5/1984 | Lubecki et al. | 378/47 |
| 4,464,330 | 8/1984 | Speir et al. | 376/159 |
| 4,783,253 | 11/1988 | Ayres et al. | 209/2 |
| 4,783,263 | 11/1988 | Trost et al. | 210/638 |

OTHER PUBLICATIONS

Assink, J. W. and Van Den Brink, Contaminated Soil, First International TNO Conference on Contaminated Soil, 11–15 Nov. 1985, Utrecht, The Netherlands.

Outokumpu Electronics Brochure, Princeton Gamma-Tech, Inc. A Member of the Outokumpu Group, Princeton, NJ, Kirjapaino Lars Eriksen Oy 1988.

Parsignault, et al., A Prompt Gamma-Ray Coal Analysis System, Conf-710402, vol. III, Neutron Sources and Applications, Proceeding of the American Nuclear Society National Topical Meeting, Apr. 19–21, 1971, Augusta, GA Sessions III & IV.

B. D. Sowerby, On-Line and Bulk Analysis of Coal and Metalliferious Obus, Journal of Radioanalytical and Nuclear Chemistry Articles, vol. 123, pp. 60–74.

Wang, et al., X-ray Fluorescence Calibration with Partial Least-Squares, Applied Spectroscopy, vol. 44, No. 6, 1990, pp. 998–1002.

Primary Examiner—Brooks H. Hunt
Assistant Examiner—Daniel J. Jenkins
Attorney, Agent, or Firm—G. H. Telfer

[57] ABSTRACT

The concentrations of residual heavy metal contaminants in the particulate material in a slurry produced in a particulate material washing process are monitored on-line and can be used to control the washing process. In alternative embodiments of the invention, x-rays, thermal neutrons or laser beams are directed at the slurry as it flows through a flow cell to induce emission of secondary x-rays, gamma rays or light, respectively, characteristic of the heavy metal contaminants and constituents representative of the solids contents of the slurry. These characteristic energies are measured and used to determine the concentration in ppm of the residual heavy metal contaminants in the particulate material within the slurry.

16 Claims, 4 Drawing Sheets

SYSTEM AND METHOD FOR ON-LINE MONITORING AND CONTROL OF HEAVY METAL CONTAMINATION IN SOIL WASHING PROCESS

RELATED APPLICATION

U.S. patent application Ser. No. 07/529,092 filed May 25, 1990 entitled "Method and Apparatus for Cleaning Contaminated Particulate Material."

BACKGROUND OF INVENTION

1. Field of Invention

This invention relates to a system and method for monitoring and controlling the level of heavy metal contamination in the slurry of a soil or other particulate material washing process.

2. Background of the Invention

Contamination of soil and other particulate materials, such as for instance sludges, sediments, scrap yard dust and the like, is becoming a more common environmental problem. Often the particulate material is contaminated with heavy metals such as, for instance, cadmium, copper, lead, mercury radium, uranium and thorium.

Various methods and systems have been developed for reducing the concentration of these heavy metal contaminants in the particulate material to acceptable levels, typically well below 1000 ppm and generally below 100 ppm. One such technique is disclosed in commonly owned related patent application Ser. No. 07/529,092 filed May 25, 1990 and entitled "Method and Apparatus for Cleaning Contaminated Particulate Material." In this process, the soil or other particulate material is first washed with a leachate or surfactant to mobilize soluble and dispersible contaminants. Large particles are mechanically separated, washed and returned to the site. The fines in which the heavy metals are concentrated, are together with the leachate and solubilized contaminants, then separated from the intermediate sized particles by a counterflow of washwater to produce a waste slurry which is disposed of or further treated. The slurry of separated intermediate sized particles and wash water is dewatered to produce additional recovered particulate material. The size of the fines separated from the intermediate sized particles can be varied (more fines recovered with the intermediate sized particles or more diverted in the waste slurry) to adjust the level of contamination remaining in the recovered particulate material.

There is a need for a reliable on-line system and method for monitoring the concentration of the heavy metal contaminants in the recovered particulate material for assuring that the required reduction in contamination level has been realized and to control the process to achieve such a result.

One of the difficulties is that it is the residual concentration of the heavy metal contaminants in the recovered particulate matter which must meet the required standards, not the slurry. There is a further need therefore for such a system and method which can determine on-line the concentration for residual heavy metal contaminants in the solids fraction of a slurry.

SUMMARY OF THE INVENTION

These and other needs are satisfied by the invention which is directed to a system and method for on-line measurements and control of the concentration of heavy metal contamination in a soil or other particulate material washing process in which a slurry of washed particulate material having residual heavy metal contamination is produced. In order to determine the concentration of the residual heavy metal contamination in the particulate material in the slurry, energy is applied to the slurry at a level to produce electromagnetic radiation which is characteristic of the constituents of the slurry including at least the residual heavy metal contaminants. The electromagnetic radiation is analyzed to measure the amount of heavy metal contaminants and the amount of particulate material in the portion of the slurry to which the energy has been applied and from these amounts the concentration of residual heavy metal contaminants can be determined.

In accordance with one embodiment of the invention, the energy is applied to the slurry in the form of x-rays at a wavelength which causes secondary emission or x-ray fluorescence of the heavy metal contaminants. The Compton scatter at wavelengths adjacent the characteristic wavelength emitted by the heavy metal contaminant is also determined and used as a measure of the mass of the particulate material irradiated which in turn is used to calculate the concentration of the heavy metal contaminant in the recovered particulate material.

In another embodiment of the invention, employing prompt neutron activation, energy is applied to the slurry by a thermal neutron field. Thermal neutrons captured by nuclei of elements in the slurry transmute the element to another isotope in an excited state. These nuclei de-excite promptly emitting gamma rays. The residual heavy metal contaminants emit gamma rays of readily identifiable characteristic energies. The magnitude of gamma rays at the characteristic energy levels is a measure of the number of atoms of the heavy metal contaminant present in the slurry within the neutron field. The hydrogen in the water phase of the slurry also emits gamma rays of characteristic energy levels, so that the water content of the slurry can be determined. The mass of particulate material is determined using a density measurement and the amount of water present. This prompt neutron activation technique measures the concentration of residual contaminants in a larger volume than the x-ray fluorescence technique which can only measure contamination near the surface of the slurry.

A third embodiment of the invention employs laser induced breakdown in which energy is applied to the slurry through a laser beam causing dielectric breakdown of the elements in the slurry which in turn emit light of characteristic energies. Characteristic light emitted by the heavy metal contaminant and reference elements which have been established statistically from samples to be substantially uniformly present in the particulate matter being treated, is measured and used to calculate the concentration of the heavy metal in the particulate material.

As another aspect of the invention, a neural network trained with slurry samples with varying concentrations of contaminants and varying water content can be used to analyze the characteristic emitted radiation. When used to control the soil washing process, the network need only output a signal indicating whether the concentration of contaminant in the particulate material fraction of the slurry is within or not within, with an appropriate margin, a specified required level.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

The present invention is directed to an on-line system for monitoring, and if desired, control of a particulate material washing processing which produces as a product of remediation a slurry. The particulate material typically would be soil, and the invention will be described as applied to a soil washing process. However, the invention may be applied to processes for remediation of other types of particulate material such as sludges, sediments, scrap yard dust and the like.

Figure 1:
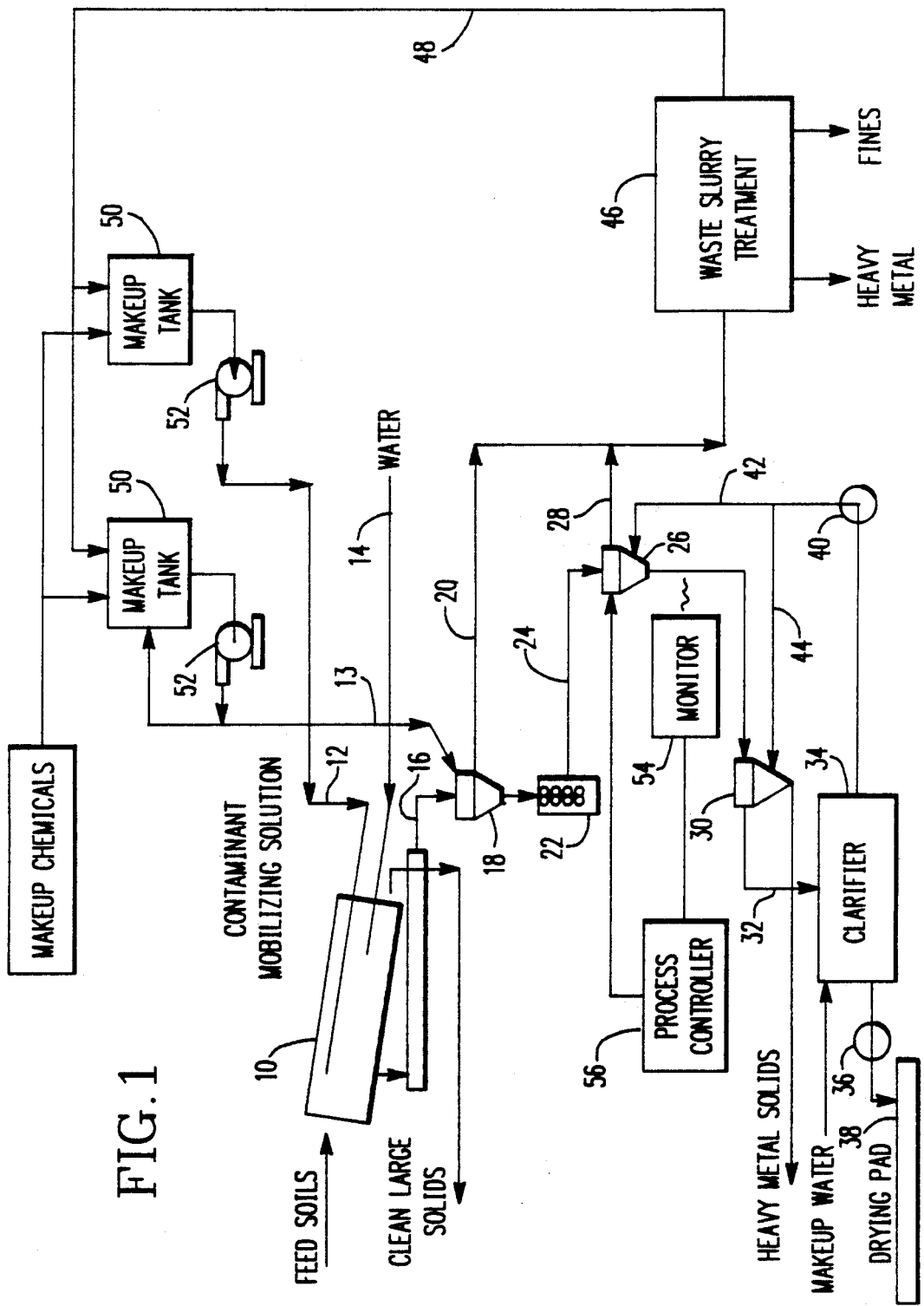
FIG. 1 is a schematic diagram of a soil washing process incorporating the invention.

A typical soil washing process is illustrated in FIG. 1. This process is described in detail in commonly owned U.S. patent application Ser. No. 07/529,092 filed on May 25, 1990 which is hereby incorporated by reference into this application. The process is designed to remove from the soil heavy metals and organics. Heavy metals removed by the process include, but are not limited to, cadmium, copper, lead, mercury, and radioactive species such as radium, uranium and thorium. Prior to the process illustrated in FIG. 1, excavated soil is processed to remove large rocks and debris. The soil is then processed n a mechanical size separator 10 to sort and prewash the feed sil with a leachate provided through a line 12. Large pieces of soil, for instance larger than 5 mm, are washed with a leachate, rinsed with water supplied through lien 14, checked for residual contaminants, and returned to the site as recovered soil.

The effluent of soil particles smaller than 5 mm and the leachate solution discharged from the mechanical separator 10 through line 16 is then processed in a counter-current flow size separator such as the mineral jig 18. In the jig 18, additional leachate solution supplied through line 13 flows upwardly counter-current to the effluent. The fines are carried upwardly with the upward flow of the leachate solution to form a slurry which is discharged through a line 20. These fines typically include heavy metal particles. The velocity of the upward flow of contaminant containing solution in the mineral jig 18 is set to separate fines of a desired size, for example fines smaller than 60 microns in diameter. The slurry discharged in the line 20 includes, in addition to the fines, leachate solution which contains solubilized heavy metals.

The intermediate sized particles between 5 mm and 60 microns in diameter, which are discharged from the bottom of the mineral jig 18, are abraded in an attrition scrubber 22 which dislodges mineral slim or fines from them. Intermediate sized particles and the dislodged fines discharged from the attrition scrubber 22 through line 24 are rinsed in a second counter-current flow size separator such as the second mineral jig 26 operated in the manner discussed above in connection with the jig 18. The counter-current flow in the second mineral jig 26 is wash water which flows upwardly at a velocity, again selected to separate the dislodged fines, typically of 60 microns in diameter and smaller. This waste slurry of fines and washwater is discharged through line 28.

The remaining intermediate sized particles discharged from the second mineral jig 26 are processed in a density separator such as a cross-current flow jig 30 to extract higher density heavy metal solid waste particles. The cross-current flow carrying the intermediate sized soil particles is discharged through a line 32 into dewatering apparatus such as for instance a clarifier 34 or a hydroclone. Sludge from the clarifier 34 is pumped by a pump 36 onto a drying pad 38. The dried particles recovered from the drying pad are checked for cleanliness and returned to the site as additional clean soil. Water removed from the clarifier 34 is circulated by a pump 40 through a line 42 as the counter-current washwater for the second mineral jig 26, and through line 44 as the cross-current flow for the density separator jig 30.

The two waste slurry streams in the lines 20 and 28 from the first and second mineral jigs 18 and 26, respectively, are discharged into a waste slurry treatment system 46 which precipitates out the dissolved heavy metals for removal with or separately from the fines for disposal or further treatment, and recirculates the leachate through line 48 to makeup tanks 50 for recirculation by pumps 52.

The soil washing process must be operated to meet the remediation levels required by environmental agencies. It is desirable to analyze the soil slurry before the costly dewatering step, to determine if the process is meeting these standards. Thus, in accordance with the invention, a monitor device 54 downstream of the mineral jig 26, analyzes the slurry of intermediate sized particles and washwater to determine whether environmental standards on the concentration of heavy metals has been met. If not, a process controller 56 responds to the monitor and adjusts the counter-current flow in the jig 26. For instance, if the heavy metal concentration in the particulate fraction of the slurry exceeds the set point value, the counter-current flow in the jig 26 is increased to divert more of the fines which typically contain the heavy metals, into the waste slurry line 28, thereby reducing the concentration of heavy metal in the slurry discharged by the jig 26. The process controller 56 could also modify the operation of the mineral jig 18 if desired. Furthermore, a monitor 54 could be located at other points in the process in place of, or in addition to, the location shown in FIG. 1.

Figure 2:
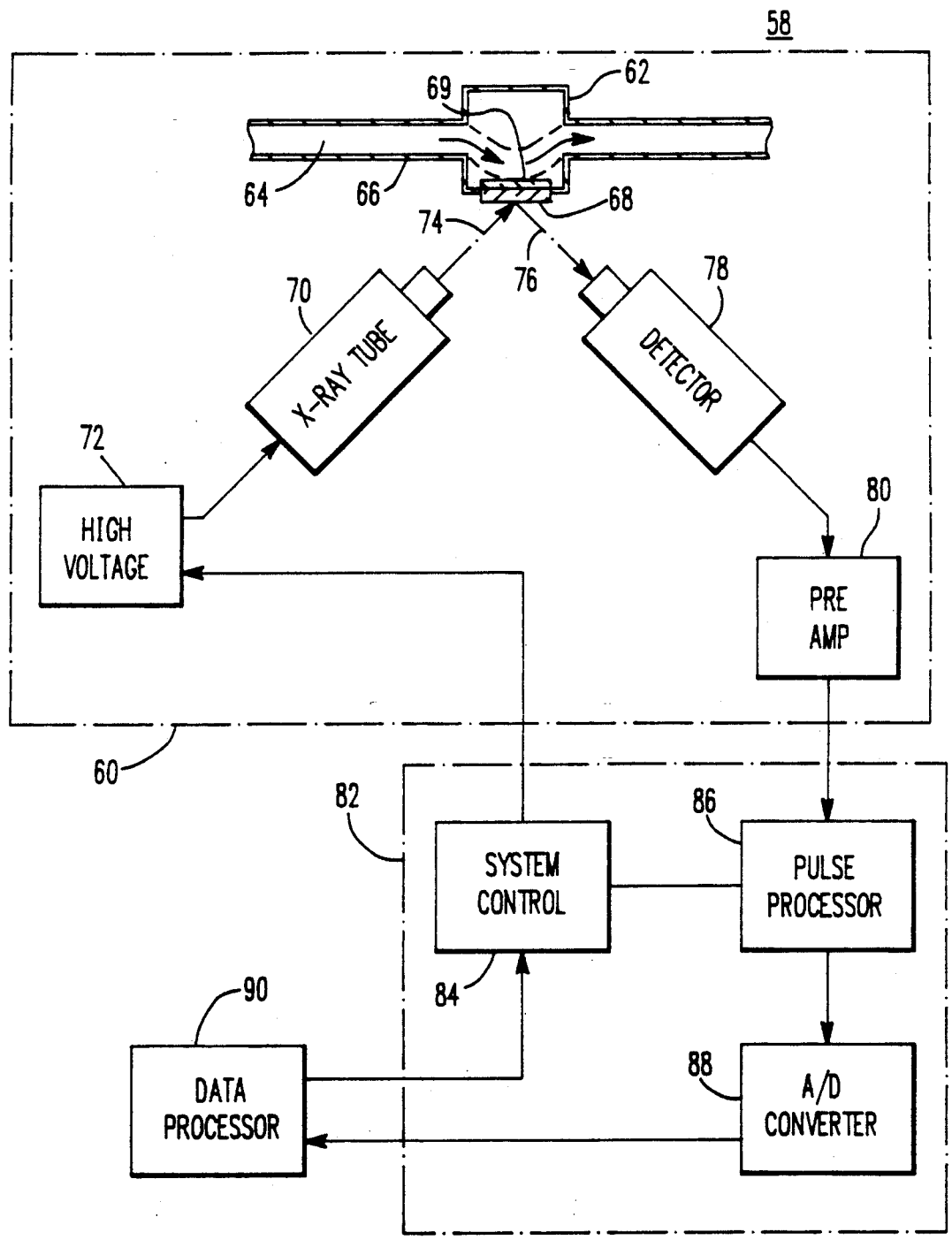
FIG. 2 is a schematic diagram of a monitoring system in accordance with one embodiment of the invention which is incorporated into the soil washing process of FIG. 1.

One embodiment of the monitor 54 is the x-ray spectrometer system 58 illustrated in FIG. 2.

The spectrometer system 58 includes a sensor module 60 which contains a flow cell 62 through which a stream of slurry 64 diverted from the main flow of the soil washing process by conduit 66 is caused to flow past a window 68 which is transparent to x-rays. An x-ray tube 70 powered by a high voltage supply 72 directs a beam of x-rays 74 through the window 68 into the slurry 64. The x-rays 74 cause secondary emission or x-ray fluorescence of the heavier elements in the slurry 64 including heavy metal contaminants. These secondary emission x-rays 76 are detected by a detector 78 which generates an electrical signal proportional to the amplitude of the secondary x-rays which is amplified in a preamplifier 80.

A control module 82 includes a system control 84 which controls the high voltage power supply 72. Module 82 also includes a pulse processor 86 which processes the signal generated by the preamp 80 and analog to digital converter 88 which digitizes the processed detector signal for input to a data processor 90. The data processor analyzes the detector signal to determine the concentration of contaminants in the slurry 64. The data processor 90 also controls the system control 84.

A key feature of the invention is the determination of when the soil washing process is running out of specifications. The x-ray fluorescence spectrometer system 58 measures the magnitude of the secondary emission of x-rays of energy levels characteristic of the contaminant of interest. The slurry though is not a representative sample of the desired product. Rather, the soil in the slurry is the desired sample, but it is a variable component of the slurry. The soil in the slurry varies in at least two ways. First, the solids content of the slurry varies. In a soil washing process, the soil content can vary from about 5% to 40% by volume or more, although for a particular soil washing process for treating soil from a particular site, the solids content will remain fairly constant at a specific location in the process. In addition to the variations in the solids content of the slurry, the soil can also vary in chemical composition. In order to determine the concentration of the contaminant, i.e., the ppm, it is necessary to also have a measure of the solids content of the sample being irradiated.

In accordance with the invention, the magnitude of the line in the energy spectrum of the secondary emissions of the characteristic energy of the contaminant of interest is measured to determine the amount of the contaminant present. The solids content is measured in accordance with one aspect of the invention by measuring the Compton scatter adjacent the characteristic energy of the contaminant of interest. Water in the slurry generates little scatter, thus, the solids content can be measured as a function of the Compton scatter. The characteristic wavelength of the contaminant of interest and the Compton scatter can be measured using an energy dispersive x-ray spectrometer as the detector 78. The magnitude of the background scatter adjacent the characteristic energy of the contaminant of interest is easily measured in this instance. Alternatively, a wavelength dispersive x-ray spectrometer could be used for this purpose. In this case, a detector for the wavelength of the contaminant of interest and a separate detector for a wavelength adjacent the wavelength of the characteristic wavelength of the contaminant, but not the wavelength of any element present in the slurry, is used to detect the background. The wavelength dispersive spectrometers provide more accurate measurement but require separate detectors for each of the wavelengths to be measured which makes them less flexible and more expensive for analyzing soils from different sources for different contaminants.

The x-ray spectrometer system 58 is calibrated for a particular site using a number of samples with varying concentrations of the contaminant and varying solids contents. Once calibrated, the system can be used on-line to monitor the soil washing process in the manner described above.

In accordance with another aspect of the invention, the solids content of the slurry is measured by measuring the amount present in the slurry of selected elements which are present substantially homogeneously in the soil being processed. In accordance with this approach, a number of samples of the slurry with varying levels of contamination and varying solids contents are analyzed for the contaminant of interest and several elements likely to be present more or less homogeneously throughout the soil. The data from these test runs are analyzed using mathematical techniques such as partial least squares and the method of principal component regression, which are well known in the field of analytical chemistry, to determine which lines are representative of the amount of soil present in the slurry. Such representative elements would be dependent on the particular soil as determined from these tests, but exemplary constituents could be: rare earths, silicon iron and aluminum.

In another embodiment of the invention, the data processor 90 includes a neural network which applies a pattern-recognition approach to determining the concentration of contaminants in the soil present in the slurry. In such an approach, the neural network is exposed to a training set of samples that represent the variation of elemental composition that is expected to be observed during the monitoring period. The neural network is also "trained" by being given the information that the contaminant is present at a concentration that is above or below the desired remediation level. In this way, the neural network "learns" to interpret the x-ray fluorescence spectra of contaminated soils, after cleaning, and to report whether the process is within specifications or out of specifications. This is the minimum information necessary for soil cleaning process control. The advantages of the pattern recognition approach are that the neural network may be tolerant of unexpected deviations in soil composition that were not represented in the training set, and that the neural network may perform adequately with minimal information that would be inadequate for a more mathematically rigorous calibration technique.

Another aspect of the invention is directed to the window 68 in the flow cell 62 of the x-ray spectrometer system 8. This window is subject to abrasion by the soil particles in the slurry 64. We have found that a thin diamond film 69 applied to the inner surface of the window 68 or even free-standing diamond film windows provide suitable erosion resistance. At the same time, the polycrystalline diamond being carbon with an atomic number of 6 is substantially transparent to x-rays. Commonly owned U.S. patent application Ser. No. 07/600,952, filed on Oct. 22, 1990 and entitled "Diamond Coated Optical Window and Methods of Making Same," discloses diamond coated windows in which a polycrystalline diamond film is deposited on a substrate. The free surface of the film is then bonded to the window material using a chalcogenide glass. The substrate is then removed. Suitable chalcogenide glasses for securing an erosion resistant layer to an optical window are disclosed in U.S. Pat. No. 4,072,782.

Figure 3:
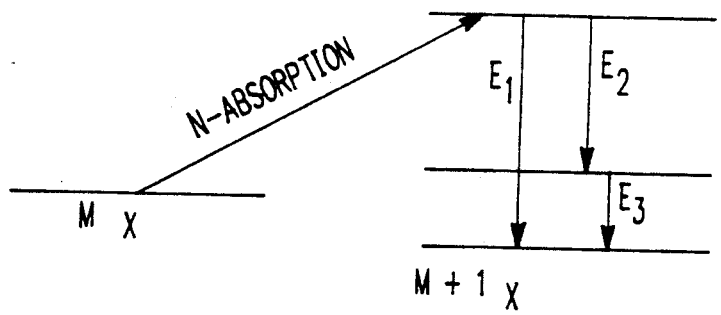
FIG. 3 is an energy level diagram associated with a second embodiment of a monitoring system in accordance with the invention.

Another embodiment of the invention is based on prompt neutron activation (PNA). The basis of the PNA approach is the thermal neutron capture reaction which is expressed symbolically by the following: $^{M}X$ (n,α) $^{M+1}X$. In this reaction, a nucleus of the element X with a mass of M captures a thermal neutron transmuting it to another isotope of X with a mass M+1. The latter nucleus is in an excited state when it is formed and it will de-excite promptly ($<10^{-6}$ sec) to the ground state by emission of gamma rays. This can be seen more clearly from the energy level diagrams of FIG. 3. These diagrams show the transition after neutron capture to an excited state in the isotope $^{M+1}X$ from which the de-excitation proceeds directly to the ground state with the emission of a gamma ray with energy $E_1$ or through intermediate levels which result in gamma rays with energies $E_2$ and $E_3$. The probability of the emission of these gamma rays, or branching ratio, is well known so that the coupling of their energies and rates of emission provide signatures of the isotope $^{M+1}X$ and also, via the reaction which produced it, of the isotope $^{M}X$.

The activation rate A, i.e., the number of these reactions per second, is governed by the equation:

$$A = n\sigma\phi \qquad Eq. 1$$

where
n is the number of target nuclei,
σ is the neutron capture cross section in cm², and
φ is the thermal neutron flux in n/cm²/sec.

The two parameters which can be controlled in this equation are n and φ, so that, basically, the PNA system should be designed to irradiate a large n with a high φ. The emission rate of gamma rays is determined by multiplying the activation rate A by B, the branching ratio for a particular gamma ray.

The complete equation for the system must factor in the gamma ray attenuation in the material between its point of origin and a gamma ray detector, the solid angle of the detection system and the efficiency of the detector for producing a full energy response to the intercepted gamma ray and may be stated as follows:

$$C = n\sigma\phi BaEG \qquad Eq. 2$$

where
C is the counting rate in counts/sec,
B is the branching ratio (unitless),
α is the attenuation factor (unitless),
E is the efficiency of a gamma ray detector, and
G is the solid angle presented by the detector array.

There are three basic elements required for PNA system operation: a thermal neutron field for the irradiation, a means for transporting the material into and out of the thermal neutron field, and a detection system for detecting the gamma ray response of the material to the thermal neutron field. Shielding, although not directly related to the system's operation, is required as well.

Thermal neutron fields for activation analysis are produced by moderating fast neutrons from a source to thermal energies. Basically, there are two types of sources: machine and isotope. Machines are available which produce neutrons of about 3 MeV. The main advantages of machines are that they produce no background gamma ray radiation, per se, and they can be turned off. Their disadvantages are that they are bulky, consume large amounts of power and are expensive (initial expense plus cost of replacement tubes). Thus, except for limited applications, an isotopic source is preferred. The leading candidate is $^{252}Cf$ which produces a fission distribution of neutrons at the rate of $2.34 \times 10^{12}$ n/sec/gm. Because of this high rate one can obtain a significant neutron emission rate for a small quantity of material. Typically, they are encapsulated in a stainless steel or zinc alloy cylinder with the dimensions, ⅜ in. diam. and about 1.5 in. length. The small size makes it particularly suitable for field applications where bulk and weight must be kept at a minimum. Two disadvantages are that $^{252}Cf$ is also an intense source of gamma rays and that it cannot be turned off.

To obtain the thermal neutron field, the high energy source neutrons must be moderated to thermal energies, i.e., energies around 0.025-0.04 eV. At these energies, a neutron is as likely to gain kinetic energy as to lose it in a collision with a nucleus. As well, at these energies, the neutron capture cross section is high, thereby enhancing the probability of a capture reaction.

Moderation is typically accomplished by surrounding the source with hydrogenous material, e.g., water, polyethylene, parraffin, etc. However, in this instance where the sample material is a waterbased slurry and a determination must be made of the solids content of the slurry, the introduction of additional hydrogenous material is to be avoided. Instead, deuterium which has a very small capture cross section is the preferred moderator.

Figure 5:
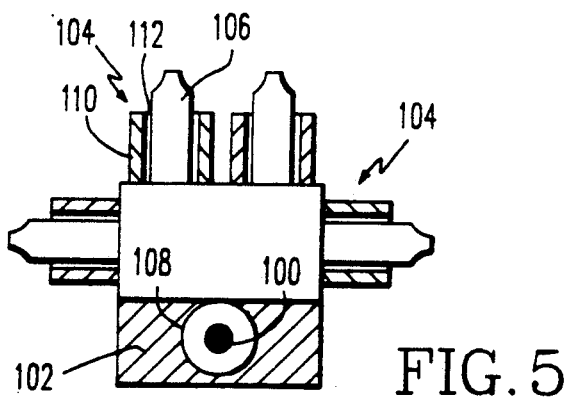
FIG. 5 is a vertical section through the monitoring system of FIG. 4 taken along the line V—V.
Figure 4:
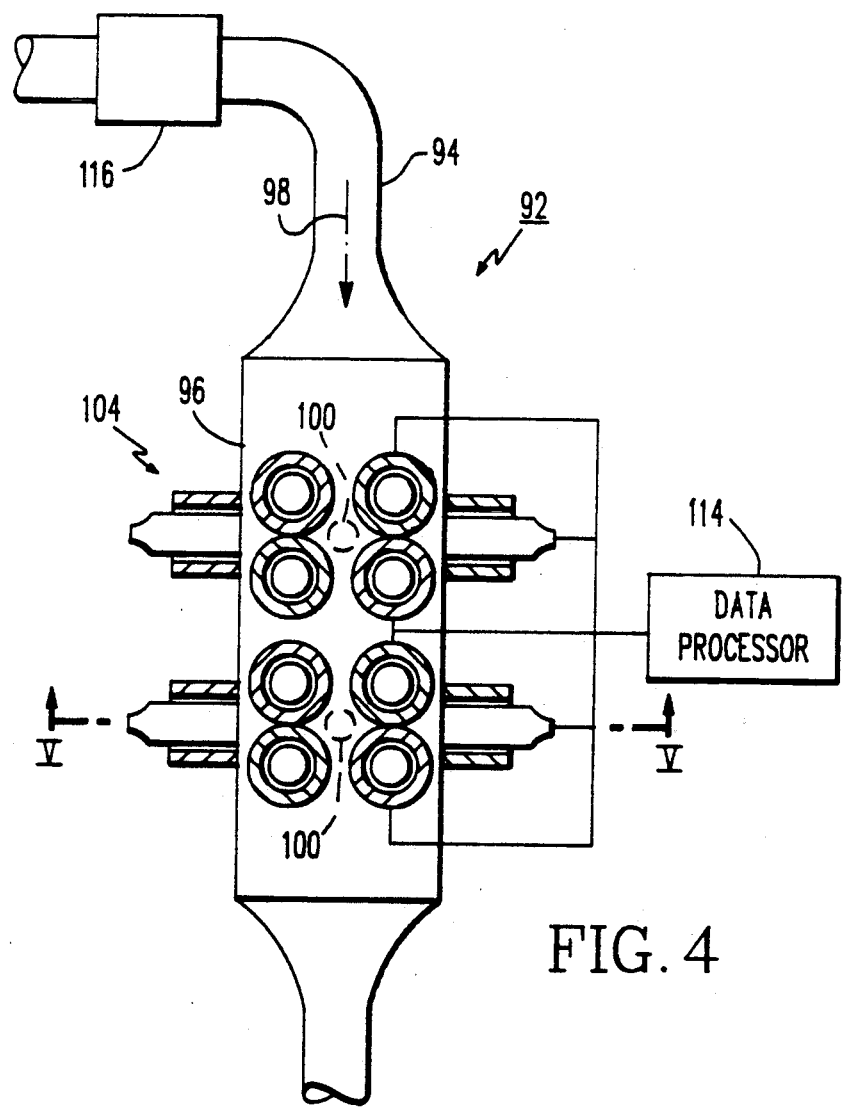
FIG. 4 is a top plane view with part in section of a monitoring system in accordance with the second embodiment of the invention.

A spectrometer system employing prompt neutron activation (PNA) system 92 is shown in FIGS. 4 and 5. In PNA system 92, a sample of the slurry is delivered through a conduit 94 to a rectangular measurement chamber 96. The chamber 96 is preferably oriented for vertical flow of the slurry 98 to prevent build-up within the chamber. A pair of $^{252}Cf$ sources 100 are spaced along one side of the measurement chamber 96 and surrounded by deuterium moderator material 102. A series of gamma ray detector elements 104 are mounted around the measurement chamber 96. Preferably, reverse electrode germanium detectors with energy resolution of few KeV for MeV gamma ray energies are used. Protection should be provided from background gamma ray radiation. One source of such background radiation is the $^{252}Cf$ neutron source 100. Accordingly, the source 100 is encapsulated in a gamma ray shield 108. Virtually any heavy metal could be used as a shield, however, bismuth is superior because of its very small neutron capture cross section and its relatively low energy gamma ray emission. Another technique would be to position the detector assemblies 104 such that they do not "face" the neutron sources 100. The detector assemblies 104 further include bismuth shielding 110 around the annular detector elements 106 which will further reduce the $^{252}Cf$ background, as well as any moderator produced background. In order to further diminish the background and enhance detector sensitivity, an annular gamma ray detector 112 is provided between the primary gamma ray detector 106 and the bismuth shield 110. The counts generated by the individual detector assemblies 104 are transmitted to a data processor 114. The data processor 114 can employ anti-coincidence techniques to eliminate pulses occurring simultaneously in the annular detectors 112 and primary detectors 106 due to gamma rays entering from the side, such as from the moderator. Furthermore, this technique would also eliminate single and double escape pulses, thereby cleaning up the spectrum.

The data processor 114 processes the signals from the detectors 104 to determine the number of atoms of the contaminant of interest in the measurement volume. Since the hydrogen atoms in the water of the slurry also emit gamma rays of a characteristic energy, the number of hydrogen atoms, and therefore the amount of water in the measurement volume can also be calculated by the data processor 114. By utilizing a density measurement, taken for instance by a weighing device 116 in the supply conduit 94, the solids content of the slurry can be calculated. With the solids content, and the amount of residual contamination detected, the concentration of the residual contamination can be determined.

An evaluation of the system disclosed in FIGS. 4 and 5 can only be made with any accuracy when the type of waste material and the potentially hazardous element composition had been identified. For purposes of illustration, it will be assumed that the soil is to be examined for traces of heavy metals, for instance, U, Th, Cd, Cu, and Pb. The U.S. EPA guideline limits for concentrations of Cd, Cu and Pb in soil are 3, 170 and 50 ppm, respectively. The limits for U and Th are given in activity concentration and are 30 and 23 pCi/gm, respectively.

A review of the neutron capture cross sections of the elements mentioned above, and their concentrations indicate that Pb will be among the most difficult to detect. The discussion will focus on that element and present the results for the others in a table. The goal in these calculations is to determine whether the PNA system disclosed in FIGS. 4 and 5 can detect the metals at the concentration levels mentioned above.

It is assumed that the soil is a slurry with a particulate concentration of 15% by volume. It is further assumed that the measurement chamber 96 is a rectangular parallelepiped with a height of 15 cm, width 30 cm and a length of 60 cm in the direction of flow.

The $^{252}$Cf sources 100 are 800 μgm each. This will produce an average thermal flux of about $10^7$ n/sec throughout the volume of the measurement chamber 96. Twenty germanium gamma ray detectors 106, each 65 mm in diameter are deployed about the volume 96. Using the count rate Equation 2 above, it is estimated that a 50 ppm concentration of Pb will give about 2-3 cts/sec. of 7.4 meV gamma rays. This is slightly low for determination of whether the soil would meet U.S. EPA guidelines; however, this approach would easily meet New Jersey's 400-1000 ppm and California's 1000 ppm guidelines. It is estimated that with small modification of the source strength or configuration that the 50 ppm level, the U.S. EPA level can be made to produce an acceptable gamma ray count rate taken to be about 10 cts/sec or more.

Table 1 presents the detection limits of the five metals mentioned above. It is arbitrarily been assumed that approximately 10 cts/sec. as a reasonable counting rate to obtain the sensitivity limit indicated. The table indicates that the system of FIGS. 4 and 5 is expected to meet the U.S. EPA guidelines for Pb and U with the system operational parameters given. For other elements listed, the detection sensitivities are far superior to the requirement of the U.S. EPA guidelines.

TABLE 1

| | Sensitivity+ of Proposed PNA System to 5 Hazardous Elements | |
|---|---|---|
| Element | U.S. EPA Soil Concentration Element | Expected PNA Sensitivity |
| Pb | 50 ppm | ≈50 ppm |
| U | 30 pCi/gm | 30 pCi/gm |

TABLE 1-continued

| | Sensitivity+ of Proposed PNA System to 5 Hazardous Elements | |
|---|---|---|
| Element | U.S. EPA Soil Concentration Element | Expected PNA Sensitivity |
| Th | 23 pCi/gm | 5 pCi/gm |
| Cd | 3 ppm | 0.35 ppm |
| Cu | 170 ppm | 8.21 ppm |

+Assumes soil to be 15% of the slurry volume; dry soil sensitivities should be better than those listed.

+Assumes soil to be 15% of the slurry volume; dry soil sensitivities should be better than those listed.

The determination of the amount of particulate material present in the slurry can alternatively be measured by measuring the magnitude of gamma rays emitted by constituents which are present in the particulate material substantially homogeneously, as discussed above in connection with x-ray fluorescence.

The prompt neutron activation system provides a determination of the residual contaminant concentration for the entire volume within the measurement chamber, while the x-ray fluorescence technique only examines the sample to a depth of about 100 microns to about 1 mm. As long as the x-ray fluorescence sample is representative of the slurry it can provide suitably accurate concentration calculations.

Figure 6:
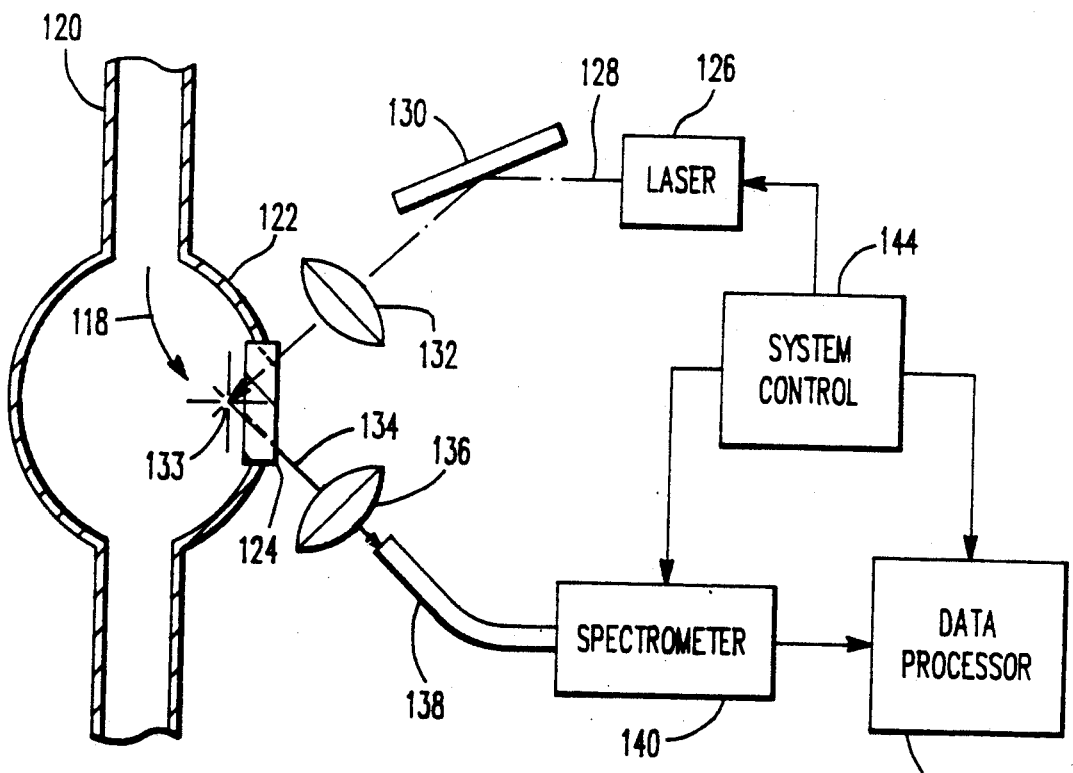
FIG. 6 is a schematic view of a third embodiment of a monitoring system which is incorporated into the soil washing process of FIG. 1.

Another embodiment of the invention is illustrated in FIG. 6. This embodiment utilizes laser induced breakdown (LIB) with spectroscopic analysis. A sample of the slurry 118 provided through conduit 120 is passed through a flow cell 122 having an optical window 124. A high power laser 126 generates a laser beam 128 which is guided by deflecting mirrors 130 (or a light guide), and focused by a lens system 132 through the window 24 onto the slurry 118. The high electric field of the focused laser pulse produces a bright hot spark through dielectric breakdown of the slurry. Light 134 from the laser induced spark 136 is collected by a lens 136 and focused onto the end of an optical fiber 138 which transmits the light to the entrance slit of a spectrometer 140. The spectrometer 140 measures the intensity of light characteristic of the contamination of interest. In order to determine the concentration of the residual contaminant, the spectrometer 140 also measures the intensity of light characteristic of elements which are ubiquitous in the soil as a measure the amount of soil vaporized in the laser beam. The selection of these reference elements and the concentration of the residual contaminant can be performed using the techniques described above in connection with the x-ray fluorescence spectroscopy. The spectrometer 140 provides the measurement of the intensity of the selected light energy to a data processor 142 which calculates the concentration of residual contaminant in the soil. A system control 144 controls the laser 126, spectrometer 140 and data processor 142. The monitoring system illustrated in FIG. 6 will generate large amounts of data at a high rate. Consider a laser firing at 100 shots per second, and a detector with 1000 channels of intensity data at 12 bit resolution. The minimum data rate to handle such data would require a capacity for 300 kbytes/sec. The requirement for calculating averages and concentrations places even greater demands on the analysis system. Thus, a workstation type computer is used as the data processor 142.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A system for washing particulate material, including soil, contaminated with heavy metal contaminants, said system including means treating said particulate material with a leachate to solubilize said heavy metal contaminants, and means separating said leachate and solubilized heavy metal contaminants from said particulate material using a flow of water to generate a waste stream of leachate solubilized heavy metal contaminants, fines of the particulate material and water, and a separate flow of a slurry of water and particulate material having residual heavy metal contaminants in a concentration of less than about 1000 ppm of particulate material, the improvement comprising:

means for on-line monitoring of the concentration of said residual heavy metal contaminants in the particulate material in said slurry including:

means applying energy to said slurry at a level to produce characteristic electromagnetic radiation from constituents in said slurry including said residual heavy metal contaminants, and analyzing means analyzing the electromagnetic radiation produced to measure an amount of characteristic electromagnetic radiation emitted by the residual heavy metal contaminants, and an amount of electromagnetic radiation representative of the particulate material in the slurry to which said energy is applied, and determining from said amount of residual heavy metal contaminants and from the amount of radiation representative of the particulate material in the slurry, the concentration of said residual heavy metal contaminants in said particulate material;

means to control operation of one of said treating means and said separating means in response to the concentration of said residual heavy metal contaminants in said particulate material.

2. The system of claim 1 including means responsive to said concentration of residual heavy metal contaminants in said particulate material in the slurry to adjust said separating means to further reduce the residual heavy metal contaminants in said particulate material in said slurry.

3. The system of claim 1 wherein said means applying said energy to said slurry comprises apparatus applying x-rays to a flowing sample of said slurry to produce characteristic x-ray radiation from constituents in said slurry including said residual heavy metal contaminants, and wherein said means analyzing said characteristic electromagnetic radiation includes x-ray detectors.

4. The apparatus of claim 3 wherein said apparatus generating x-rays generates x-rays at a selected energy level which excites said residual heavy metal contaminants to produce said characteristic electromagnetic radiation and which produces Compton scatter radiation, and wherein said x-ray detector includes means detecting said characteristic electromagnetic radiation of said residual heavy metal contaminants, and said Compton scatter radiation, and wherein said analyzing means includes means determining from said characteristic electromagnetic radiation of said residual heavy metal contaminants and said Compton scatter radiation the amount of particulate material in said slurry.

5. The system of claim 3 wherein said means analyzing said characteristic electromagnetic radiation emitted by constituents of said slurry includes a neural network conditioned with samples of slurries having varying concentrations of residual heavy metal contaminants and particulate material for determining on-line the concentration of residual heavy metal contaminants in said slurry.

6. The system of claim 1 wherein said analyzing means includes a neural network conditioned with slurry samples containing varying concentrations of residual heavy metal contaminants and particulate material for determining on-line the concentration of residual heavy metal contaminants in said particulate material in said slurry.

7. The system of claim 3 including a flow cell through which a flow of said slurry is directed, said flow cell having a window transparent to said x-rays and comprising at least on an inner surface of said window facing said flow of said slurry a polycrystalline diamond film.

8. The system of claim 3 wherein said analyzing means measures the magnitude of x-rays produced by constituents present substantially homogeneously in the particulate material and determines therefrom the amount of particulate material present in said slurry for determining the concentration of said heavy metal contaminant in said particulate material.

9. The system of claim 1 wherein said means applying energy to said slurry comprises prompt neutron activation means bombarding said particulate material with thermal neutrons inducing constituents in said particulate material including said residual heavy metal contaminants to emit characteristic gamma rays and means analyzing said gamma rays to determine the magnitude of the gamma rays emitted by said residual heavy metal contaminants and the magnitude of gamma rays emitted by selected other constituents related to the amount of particulate material present in said slurry, and determining from the magnitudes of said gamma rays, the concentration of said heavy metal contaminants in said particulate material.

10. The system of claim 9 wherein said prompt neutron activation means comprises a source of fast neutrons, and a non-hydrogenous moderator slowing said fast neutrons to produce said thermal neutrons.

11. The system of claim 10 wherein said means analyzing selects as said other constituents in said slurry hydrogen in the water in said slurry and determines the magnitude of gamma rays emitted by said hydrogen for determining the amount of particulate material in said slurry.

12. The system of claim 11 wherein said analyzing means includes a neural network conditioned with samples of varying concentrations of heavy metal contaminants and particulate material in said slurry to determine from said magnitudes of gamma rays emitted by said heavy metal contaminants and by hydrogen in the water in said slurry, the concentration of heavy metal contaminants in the particulate material.

13. The system of claim 9 wherein said analyzing means selects as said other constituents in said slurry, constituents present substantially homogeneously in said particulate material and determines the magnitude of gamma rays emitted by said constituents present substantially homogeneously to determine the amount of particulate material in the slurry.

14. The system of claim 1 wherein said means for applying energy to said slurry comprises means directing a laser beam at a portion of said slurry to vaporize and breakdown constituents in said slurry into characteristic light, and wherein said analyzing means comprises means determining the magnitude of characteristic light emitted by said heavy metal contaminants, and characteristic light emited by constituents present substantially homogeneously in said particulate material and determining therefrom the concentration of heavy metal contaminants in the particulate material in said slurry.

15. The system of claim 14 wherein said analyzing means includes a neural network trained with a plurality of samples of said slurry with varying concentrations of heavy metal contaminants and particulate material for determining on-line the concentration of heavy metal contaminants in said particulate material in the slurry.

16. A system in accordance with claim 1 wherein:
said means to control comprises a process controller responsive to a signal from the analyzing means indicating the concentration of said residual heavy metal contaminant is outside a predetermined range to change flow conditions in said separating means.

* * * * *